US006495355B1

(12) United States Patent
Contag et al.

(10) Patent No.: US 6,495,355 B1
(45) Date of Patent: Dec. 17, 2002

(54) RED-SHIFTED LUCIFERASE

(75) Inventors: Christopher Contag, San Jose, CA (US); Brian Eames, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/602,628

(22) Filed: Jun. 21, 2000

Related U.S. Application Data

(60) Provisional application No. 60/140,598, filed on Jun. 22, 1999.

(51) Int. Cl.$^7$ .............................. C12N 15/53; C12N 9/02
(52) U.S. Cl. .................... 435/189; 435/320.1; 435/325; 435/8; 536/23.2
(58) Field of Search .................... 536/23, 2; 435/320.1, 435/325, 189, 8

(56) References Cited

U.S. PATENT DOCUMENTS 5,650,135 A   7/1997   Contag et al. ................. 424/91

FOREIGN PATENT DOCUMENTS

JP              929460       * 11/1997

OTHER PUBLICATIONS

Eames, B.F., et al. (1999) SPIE Conf. on Molec. Imaging 3600, 36–39.*
De Wet, J.R., et al. (1987) Mol. Cell. Biol. 7(2), 725–737.*
Branchini et al. (1998), "Site–Directed Mutagenesis of Histidine 245 in Firefly Luciferase: A Proposed Model of the Active Site." *Biochemistry*, vol. 37:15311–15319. (1998).
Contag et al. (1995), "Photonic Detection of Bacterial Pathogens in Living Hosts." *Molecular Microbiology*, vol. 18(4):593–603. (1995).
Contag et al. (1997), "Visualizing Gene Expression in Living Mammals Using a Bioluminescent Reporter." *Photochemistry and Photobiology*, vol. 66(4):523–531. (1997).
Hooper et al (1990), "CCD Imaging of L:ucoferase Gene Expression in Single Mammalian Cells." *Journal of Bioluminescence and Chemiluminescence*, vol. 5:123–130. (1990).
Kajiyama et al. (1991), "Isolation and Characterization of Mutants of Firefly Luciferase which Produce Different Colors of Light." *Protein Engineering*, vol. 4(6):691–693. (1991).
Kajiyama et al. (1994), "Enhancement of Thermostability of Firefly Luciferase from *Luciola lateralis* by a Singe Amino Acid Substitution." *Biosci. Biotech. Biochem.*, vol. 58(6):1170–1171. (1994).
Sung et al. (1998), "The N–Terminal Amino Acid Sequences of the Firefly Luciferase are Important for the Stability of the Enzyme." *Photochemistry and Photobiology*, vol. 68(5):749–753. (1998).
Welsh et al. (1997), "Reporter Gene Expression for Monitoring Gene Transfer." *Current Opinion in Biotechnology*, vol. 8:617–622. (1997).
White et al. (1996), "Improved Immunostability of the North American Firefly Luciferase: Saturation Mutagenesis at Position 354." *Biochem. J.*, vol. 319:343–350. (1996).
Wood et al. (May 12 1989), "Complementary DNA Coding Click Beetle Luciferases Can Elicit Bioluminescence of Different Colors." *Science*, vol. 244:700–702. (1989).
Genbank Accession No. U51019 (Jun. 28, 2000).
Genbank Accession No. M15077 (Apr. 26, 1993).
Genbank Accession No. U47298 (Feb. 24, 1996).

* cited by examiner

*Primary Examiner*—Charles L. Patterson, Jr.
(74) *Attorney, Agent, or Firm*—Pamela J. Sherwood; Bozicevic, Field & Francis LLP

(57) ABSTRACT

Nucleic acid compositions and polypeptides encoding a red-shifted form of firefly luciferase are provided. These red-shifted luciferases are characterized by spectrum of light emission having detectable emissions at 610 nm (luc$^{610}$), preferably a primary peak at 610 nm. The nucleic acid compositions find use in various systems as a reporter gene, and are of particular interest for use as a reporter with in vivo systems, because of the efficient transfer of red light through tissues. The red-shifted luciferase may be combined in such assays with luciferases emitting at other spectra, in order to monitor multiple processes simultaneously.

27 Claims, 4 Drawing Sheets

RED-SHIFTED LUCIFERASE

CROSS-REFERENCES

This application claims priority to, and incorporates by reference in its entirety, earlier filed provisional patent application No. 60/140,598 filed Jun. 22, 1999.

BACKGROUND OF THE INVENTION

Bioluminescence is the emission of light from an organic molecule, such as "luciferin", which has been oxidized by oxygen or one of its metabolites. The reaction is catalysed by a protein, usually known as a "luciferase", or "photoprotein". The luciferases of beetles and fireflies utilize benzothiazole as a luciferin. For a given photoprotein additional substances, cofactors, may be required to generate light. These may include cations (such as magnesium), or cofactors such as NADH, FMN, or ATP; a fluor may also be included as an energy transfer acceptor. Reactions involving these cofactors, luciferases and luciferins result in the emission of light, which can occur in a spectrum of colors.

Photoproteins have been used in a variety of ex vivo and in vitro assays to determine levels of gene expression, presence and concentration of contaminants or energy levels (ATP). More recently, these enzymes have been used to monitor biological processes in living cells and animals. Generally, in luminescence assays, reaction substrates and other luminescence-activating reagents are introduced into a biological system suspected of expressing a reporter enzyme. Resultant luminescence, if any, is then measured using a photomuliplier tube, a charge coupled device. or any suitable radiant energy-measuring device in the form of a luminometer or camera. The assay can be rapid and sensitive, and may provide data quickly and easily, without the need for radioactive reagents, additional contrast reagents or dyes.

The most commonly used bioluminescent reporters emit in the blue to yellow-green range (250–560 nm). However, red light is transmitted through live tissue more efficiently than other wavelengths of visible light (see Cambell (1988), "Chemiluminescence: Principles and Applications in Biology and Medicine"; and Jobis (1977)). By red-shifting the emission of bioluminescent reporters, it may be possible to enhance their utility for in vivo monitoring of biological processes, and provide additional reagents for multiparameter analysis by providing additional colors.

Multicolor functional assays have utility in analyses of coordinately regulated processes in ex vivo samples, cell lysates, living cells and living animals. Multiple colors of bioluminescent light from naturally occurring luminescent species have been identified, and in fact luciferase clones obtained from a single beetle species were shown to encode enzymes that emit at four different wavelengths (green to orange) (Wood et al. (1989) Science 244:700–702). With photoproteins that emit at different wavelengths, it may be possible to monitor multiple functions in vitro, in cells and in animals using spectrally resolved methods for analyses and imaging.

Luciferase genes are widely used as genetic reporters due to low background providing good signal to noise ratios, their non-radioactive nature, extreme sensitivity, broad dynamic range and linear response in various assays. (see, for example Welsh and Kay (1997) Curr Opin Biotechnol 8(5):617–22). Since as few as $10^{-20}$ moles of the firefly luciferase can be detected, luciferase assays for gene activity are used in virtually every experimental biological system, including prokaryotic and eukaryotic cell cultures, transgenic plants, cells and animals, and cell-free expression systems. Similarly, luciferase assays of ATP are highly sensitive, enabling detection to below $10^{-16}$ moles.

Currently, luciferase genes from a wide variety of vastly different species, particularly the luciferase genes of *Photinus pyralis* (the common firefly of North America), *Pyrophorus plagiophathalamus* (the Jamaican click beetle), *Renilla reniformis* (the sea pansy), and several bacteria (e.g., *Photorhabdus luminescens* and *Vibrio* spp), are used as luminescence reporter genes. Amino acid substitutions in the active sites of luciferase clones have been reported to alter wavelength of emission (Kajiyama et al. (1991) *Prot. Eng.* 4:691). However, red-emitting clones of a well-characterized luciferase with readily available sources of substrate have not been reported.

Relevant Literature

Engineering of luciferases has been reported. Sung and Hang (1998) *Photochem Photobiol* 68(5):749–53 disclose that the N-terminal amino acid sequences of the firefly luciferase are important for the stability of the enzyme. Branchini et al. (1998) *Biochemistry* 37(44):15311–9 performed site-directed mutagenesis of histidine 245 in firefly luciferase. White et al. (1996) *Biochem J* 319 (Pt 2):343–50. showed an improvement in the thermostability of the North American firefly luciferase by saturation mutagenesis at position 354. Kajiyama and Nakano (1994) *Biosci Biotechnol Biochem* 58(6):1170–1 constructed firefly luciferase mutants from Luciola lateralis in which Ala at position 217 was replaced by each of three hydrophobic amino acid residues (Ile, Leu,. and Val). U.S. Pat. No. 5,401,629 Harpold, et al. describes assay methods and compositions useful for measuring the transduction of an intracellular signal.

Contag et al. (1997) *Photochem Photobiol* 66(4):523–31 describes the use of bioluminescence to monitor gene expression in living mammals. Viral promoters fused to firefly luciferase as transgenes in mice allowed external monitoring of gene expression both superficially and in deep tissues. In vivo bioluminescence was detectable using either intensified or cooled charge-coupled device cameras, and could be detected following both topical and systemic delivery of substrate. U.S. Pat. No. 5,650,135, Contag, et al., entitled "Non-invasive localization of a light-emitting conjugate in a mammal" also describes the use of in vivo bioluminescence.

Contag et al. (1995) *Mol Microbiol* 18(4):593–603 describe a method for detecting bacterial pathogens in a living host; used to evaluate disease processes for strains of *Salmonella typhimurlum* that differ in their virulence for mice. Three strains of Salmonella were marked with bioluminescence through transformation with a plasmid conferring constitutive expression of bacterial luciferase. Detection of photons transmitted through tissues of animals infected with bioluminescent Salmonella allowed localization of the bacteria to specific tissues. In this manner progressive infections were distinguished from those that were persistent or abortive.

Hooper et al. (1990) *J Biolumin Chemilumin* 5(2):123–30 review low-light-level imaging, with particular reference to charge-coupled device (CCD) cameras. Detectors for sensitive imaging are described and compared, including various CCDs and photon-counting devices. Image analysis techniques based on digital image processing may be applied to quantify luminescent processes with these detectors. Images of luciferase gene expression in single mammalian cells have been obtained using a particular high-sensitivity intensified CCD camera.

DATABASE REFERENCES FOR NUCLEOTIDE AND AMINO ACID SEQUENCES

The nucleotide sequence of the optimized firefly luciferase gene present in the plasmid, pGL3, may be accessed at Genbank (no. U47298), and for convenience is provided in the SEQLIST as SEQ ID NOs:7 and 8. This sequence is based on the wild-type *Photinus pyralis* sequence, accessible as Genbank no. M15077, or in the SEQLIST as SEQ ID NOs:11 and 12. The sequence of the luciferase from *Luciola lateralis* is accessible as Genbank no. U51019, or in the SEQLIST as SEQ ID NOs:9 and 10.

SUMMARY OF THE INVENTION

Nucleic acid sequences, and predicted amino acid sequences, for mutated forms of the firefly luciferase gene are provided. Gene products from these mutated forms are characterized by an altered light emission, where the normal, or wild-type, yellow-green peak at 560 nm is shifted to a orange-red peak at 610 nm, hence a red-shift. The nucleic acid compositions and resulting enzymes find use in various systems as a reporter gene, and are of particular interest for use as a reporter in multicolor assays and with in vivo systems, because of the relative increase in tissue penetration by red light over shorter wavelengths. The luciferase mutants may be used in a range of biological investigations, including the detection, location and measurement of microbes (protozoa, bacteria, viruses); detection and location of cancer cells; measurement of enzymes, intracellular signaling and other turnover reactions in cells or fluids; DNA and RNA binding assays; immunoassays and other protein assays. The red-shifted luciferase may be combined in such assays with luciferases emitting at other wavelengths, in order to monitor multiple processes simultaneously.

DESCRIPTION OF THE PREFERRED EMBODIMENTS

Figure 1A:
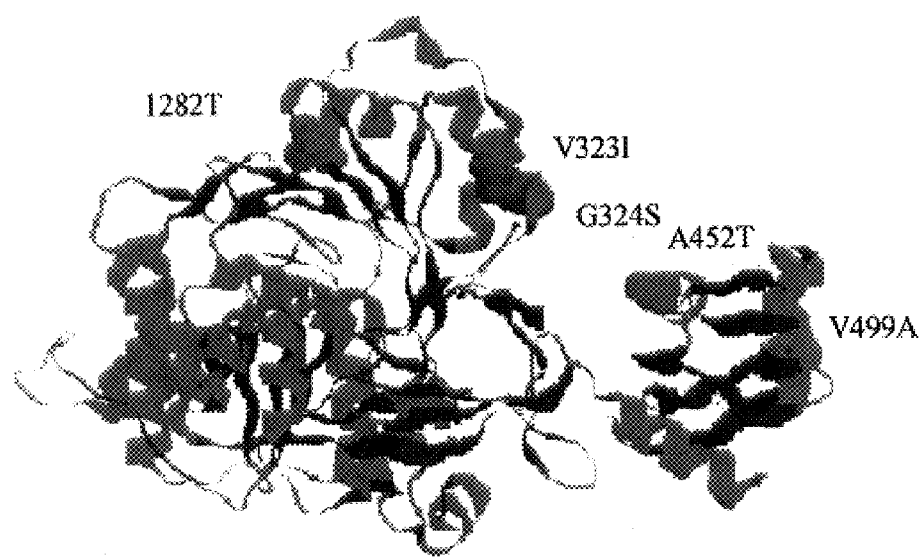
FIG. 1A shows the identification of mutated sites on the 3 dimensional structure of North American Firefly luciferase.

Nucleic acid compositions encoding a red-shifted form of firefly luciferase are provided. These red-shifted luciferases are characterized by light emission with peak emission at 610 nm ($luc^{610}$). In a preferred embodiment of the invention, the primary emission is at 610 nm. The red-shifted luciferase, $luc^{610}$, is a form of *Photinus pyralis* luciferase having amino acid substitutions from the wild-type $luc^{560}$ form, particularly at the residues corresponding to positions 323 and 324. Additional amino acid substitutions may also be present, e.g. at position 452.

The nucleic acid compositions find use in various systems as a reporter gene, and are of particular interest. for use as a reporter for multicolor and/or in vivo systems, because of the greater separation in peak emission and more efficient transfer of red light, compared to shorter wavelengths, through tissues. The luciferase. may be used in a range of biological investigations, including the detection, location and measurement of microbes (protozoa, bacteria, viruses); detection and location of cancer cells; measurement of enzymes, intracellular signaling and other turnover reactions in cells or fluids; DNA and RNA binding assays; and immunoassay and other protein assays. The red-shifted luciferase may be combined in such assays with luciferases emitting at other spectra, in order to monitor multiple processes simultaneously.

DEFINITIONS

It is to be understood that this invention is not limited to the particular methodology, protocols and reagents described, as such may vary. It is also to be understood that the terminology used herein is for the purpose of describing particular embodiments only, and is not intended to limit the scope of the present invention which will be limited only by the appended claims.

It must be noted that, as used herein and in the appended claims, the singular forms "a", "and", and "the" include plural referents unless the context clearly dictates otherwise. Thus, for example, reference to "a compound" includes a plurality of such compounds and reference to "the enzyme" includes reference to one or more enzymes and equivalents thereof known to those skilled in the art, and so forth.

All technical and scientific terms used herein have the same meaning as commonly understood to one of ordinary skill in the art to which this invention belongs unless clearly indicated otherwise. Although any methods, devices and materials similar or equivalent to those described herein can be used in the practice or testing of the invention, the preferred methods, devices and materials are now described.

Red-shifted luciferase ($luc^{610}$): as used herein, the term red-shifted luciferase or $luc^{610}$ are used interchangeably to intend a luciferase polypeptide that, in the presence of an appropriate luciferin substrate, emits light in the visible range of red light, i.e. between 610 and 700 nm. In some cases there will also be light emitted at other wavelengths, particularly at 560 nm. However, it is preferable to have the primary peak at 610 nm.

As used herein, the term luciferase genes and encoded proteins shall be used to generally designate any of the firefly luciferase genes and gene products, preferably the *Photinus pyralis* homolog. Variations in the *P. pyralis* luciferase have been described (see previous citations), and include modifications to the codons for optimal expression in mammalian cells, alteration of the peroxisome targeting sequence, stability changes in the N-terminus or at position 354, mutations at His 245, etc. One of skill in the art will appreciate that the term "*P. pyralis* luciferase" includes these and other variations in the sequence.

For reference purposes, the amino acid substitutions that result in a red-shifted luciferase will be designated according to the amino acid residues on the luciferase present in the pGL3 series of plasmids, provided in SEQ ID NO:11. In comparing to other luciferases, these sequences are readily aligned to correct for minor length variations in sequence, e.g. shortening of the polypeptide at the termini, and the like. Mutations may also be specified in terms of the DNA sequence.

Red-shifted luciferases of particular interest have amino acid substitutions at positions 323 and 324. The valine at residue 323 is substituted with an isoleucine (V323I), or other non-polar amino acids, e.g. leucine, phenylalanine, and alanine.

The $luc^{560}$ glycine at position 324 is substituted with a serine (G324S), or may be substituted with similar uncharged polar amino acids, e.g. cysteine and threonine. Such codons, e.g. V323I; G324S; G324C; G324T, etc. can be engineered into the gene sequence, through conventional recombinant DNA technology, including the methods provided in the examples, to provide proteins having the red-shifted phenotype.

In one embodiment of the invention, the luc$^{610}$ also comprises an amino acid substitution at position 452, which has the effect of enhancing the red shift, such that the primary emission peak is in the red spectrum. In screening mutations, it was found that an ala→thr (A452T) substitution at position 452 has this effect. Other polar amino acids may also be substituted at this position, e.g. serine (A452S), cysteine (A452C), glycine (A452G), etc.

Examplary are the three provided luc$^{610}$ sequences as set forth in SEQ ID NOs:1, 3 and 5. A summary of the substitutions between that in pGL3 and the red-shifted luciferases is as follows:

| | Clone | | | |
| --- | --- | --- | --- | --- |
| AA position | pGL3 (SEQ ID NO:7,8) | clone 4 (SEQ ID NO:1,2) | clone 1 (SEQ ID NO:3,4) | clone 14 (SEQ ID NO:5,6) |
| 257 | met | met | met | ile |
| 282 | ile | thr | ile | ile |
| 323 | val | ile | ile | ile |
| 324 | gly | ser | ser | ser |
| 403 | ser | ser | ser | asn |
| 434 | ile | ile | val | ile |
| 452 | ala | thr | ala | ala |
| 499 | val | ala | val | val |

The red-shifted variants of the invention were derived by in vitro mutagenesis of a cloned luciferase template. Many methods of altering genetic sequences are known and used in the art, and need not be further elaborated here. The provided nucleid acid sequences may be used in a wide variety of assays that may include gene expression studies (i.e. reporter gene) or screening purposes, as a fusion protein.

further modifications and changes may be made in the sequence of the red-shifted luciferase and still obtain a molecule having the desired characteristic of red light emission. For example, certain amino acids may be substituted for other amino acids in a protein structure without appreciable loss of function. It will be understood by one of skill in the art that various changes (such as to alter protein stability or enzyme efficiency) may be made in the sequence of red-shifted luciferase proteins without appreciable loss of their biological utility or activity. So long as a mutation or change maintains a red-shifted luciferase, the resultant protein will be considered a biologically functional equivalent for the purposes of the invention.

The polypeptide sequence may be further modified, either chemically or by genetic engineering, to enable the luciferase to be targeted into a specific subcellular compartment. For example, a suitable sequence at the N-terminus will locate the bioluminescent protein in the mitochondria, while others will target the protein to the endoplasmic reticulum, optionally with a sequence at the C terminus to retain it there. Genetically engineering the gene such that the protein contains a signal peptide can locate the protein to the inner or outer surface of the plasma membrane or within a particular intracellular organelle (e.g. peroxisome, mitochondrion, chloroplast, endoplasmic reticulum, golgi, secretory vesicle, nucleus or endosome).

Expression Vectors: Transformation, transduction or transfection of host cells with DNA segments encoding the red-shifted luciferase is used to express the recombinant luciferase in cells, and is a convenient means of monitoring activity of regulatory sequences (e.g. promoters), where the coding sequence then constitutes the reporter gene. The coding sequences derived from either cDNA or genomic sequences are suitable for eukaryotic expression, as the host cell will generally process the genomic transcripts to yield functional messenger RNA (mRNA) for translation into protein. For prokaryotes, coding sequences that lack introns will be used as they do not splice the message.

Different proteins may be co-expressed and monitored in the same cell using different colored luciferases or other reporter proteins, including green fluorescent proteins, chloramphenical acetyl transferase, beta-galactosidase, etc. This may be achieved by co-transfecting the cell with two distinct recombinant vectors, each bearing a copy of a reporter gene which may be linked to a unique promoter and/or particular protein-encoding DNA sequence. Alternatively, a single recombinant vector may be constructed to include both such coding regions which could then be expressed in cells transfected with the single vector. Such single vector transfections could be used for assays that assess protein processing such as protease activity or phosphorylation.

The term "expression vector" includes any type of genetic construct containing a nucleic acid sequence encoding a red-shifted luciferase, or other reporter gene, in which the nucleic acid sequence is capable of being transcribed and translated in a mammalian cell or cells from other organisms. The expression vectors of the invention should also direct translation into luciferase protein. Expression vectors will generally include restriction enzyme cleavage sites and the other initial, terminal and intermediate DNA sequences that are usually employed in vectors to facilitate their construction and use.

Expression vectors for use in mammalian cells ordinarily include an origin of replication (as necessary), a selectable marker and a promoter operably linked to the gene(s) to be expressed. A polyadenylation site and transcriptional terminator sequences are preferably included on genes to be expressed in target eukaryotic cells. Ribosome binding sites, internal ribosome entry sites (IRES) and RNA splice sites may also be included. An example is the SV40 late gene 16S/19S splice donor/splice acceptor signal. The origin of replication may be provided either by construction of the vector to include an exogenous origin, such as may be derived from SV40 or other viral source, or may be provided by the host cell chromosomal replication mechanism. If the vector is integrated into the host cell chromosome, the latter is often sufficient. Vectors will usually include an origin of replication functional in bacteria and a typical antibiotic resistance gene, allowing propagation and selection in transformed bacterial cells.

Specific initiation signals may also be required for efficient translation. These signals include the ATG initiation codon and adjacent sequences. Translational control signals within or outside of the luciferase coding sequence, including the ATG initiation codon, may additionally need to be provided in native or modified forms. One of ordinary skill in the art would readily be capable of determining this and providing the necessary signals. These exogenous translational control signals and initiation codons can be of a variety of origins, both natural and synthetic. The efficiency of expression is enhanced by the inclusion of appropriate transcription elements and transcription terminators. An appropriate polyadenylation site (e.g., 5'-AATAAA-3') may also be included. Typically, the poly A addition site is placed about 30 to 2000 nucleotides "downstream" of the termination site of the protein at a position prior to transcription termination. Those regulatory signals from the SV40 virus, bovine growth hormone gene, etc. are convenient and known to function well.

For long-term, high-yield production of recombinant proteins, stable expression is often preferred. In such cases host cells can be transformed with vectors controlled by appropriate expression control elements, e.g. promoter, enhancer, sequences, transcription terminators, polyadenylation. sites, etc., and a selectable marker in order to integrate into the host chromosomal DNA. Following the introduction of foreign DNA, transformed cells may be allowed to grow for 1–2 days in an enriched media, and then are switched to a selective media. The selectable marker in the recombinant plasmid confers resistance to the selection and allows cells to stably integrate the plasmid into their chromosomes and grow to form clonal colonies which can be expanded and archived as cell lines.

A number of selection systems may be used, including, but not limited to, the herpes simplex virus thymidine kinase (TK), hypoxanthine-guanine phosphoribosyltransferase and adenine phosphoribosyltransferase genes, in tk- hgprt- or aprt- cells, respectively. Also, antimetabolite resistance can be used as the basis of selection, for example using the dihydrofolate reductase (dhfr) gene to confer resistance to methotrexate; guanosine phosphoribosyl transferase (gpt) for resistance to mycophenolic acid; neomycin resistance (bacterial in origin) for resistance to the aminoglycoside G-418; hygromycin resistance (hygro) for resistance to hygromycin, and the like.

Expression vectors will comprise the luciferase coding region operably attached to a promoter, by positioning the 5' end of the transcription initiation site between about 1 and 50 nucleotides "downstream" of the chosen promoter. The "upstream" promoter stimulates transcription of the DNA and promotes expression of the encoded recombinant protein. The phrase "operable" mean that the promoter is in the correct location and orientation in relation to the red-shifted luciferase nucleic acid to control RNA polymerase initiation and expression of the red-shifted gene. The promoter used to express the red-shifted luciferase is not critical to the present invention. The use of promoters is well-known in the art.

A number of viral-derived sequences can be used in expression systems. For example, commonly used promoters are derived from polyoma viruses (e.g. SV40), Adenovirus 2 or cytomegalovirus (CMV). The early and late promoters of SV40 virus are particularly useful because both are obtained easily from the virus as a fragment which also contains the SV40 viral origin of replication. Smaller or larger SV40 fragments may also be used, as may the Rous sarcoma virus (RSV) long terminal repeat (LTR) and LTR's from other retroviruses. Selection of a promoter that is active specifically in certain cell types will permit cell- or tissue-specific expression that may be regulated temporally or in response to various stimuli. Such promoters include those from the liver fatty acid binding (FAB) protein gene promoter, specific for colon epithelial cells; the insulin gene promoter, specific for pancreatic cells; the transphyretin, .alpha.1-antitrypsin, plasminogen activator inhibitor type 1 (PAI-1) apolipoprotein AI and LDL receptor gene promoters, each directing specific or preferential expression in liver cells. Promoters active in brain tissues include the myelin basic protein (MBP) gene promoter, specific for oligodendrocytes; the glial fibrillary acidic protein (GFAP) gene promoter, specific for glial cells; and the neuron-specific enolase (NSE) promoter that is specific for neuronal cells.

Furthermore, selection of a promoter that is regulated in response to specific chemical or physiological signals can permit inducible expression of the red-shifted luciferase gene. Examples of suitable inducible promoters include the PAI-1, cytochrome P450 gene promoters, heat shock protein genes and hormone inducible gene promoters, and the fos and jun promoters inducible by ionizing radiation.

The $luc^{610}$ sequences are linked to regulatory sequences as appropriate to obtain the desired expression properties. When any of the above host cells, or other appropriate host cells or organisms, are used to replicate and/or express the proteins from the nucleic acids or nucleic acids of the invention, the resulting replicated DNA, RNA, expressed protein or polypeptide, is within the scope of the invention as a product of the host cell or organism. The product is evaluated, monitored or recovered by any appropriate means known in the art.

Reporter genes: Red-shifted luciferase can be used in a variety of assays as a reporter gene, e.g. to identify transformed cells; to measure gene expression in vitro, in vivo and ex vivo; to label specific microorganisms or cells of multicellular organisms; to label and locate fusion proteins; to study intracellular trafficking and the like. The protein may also find use in various biochemical applications, e.g. as a molecular weight marker on protein gels and Western blots, in calibration of fluorometers and FACS machines and in microinjection into cells and tissues.

The red-shifted luciferase may be used in combination with other light emitting reporter genes, e.g. fluorescent proteins, luciferases that emit light at a different wavelength or convert substrates that emit light, change color and/or fluoresce, etc. Different colored reporter genes can be used simply to identify multiple cell populations in a mixed cell culture or to track multiple cell types, enabling differences in cell movement or migration to be visualized in real time. Other embodiments include tracking and determining the location of cells or multiple proteins within a single cell, tissue or organism; differential promoter analyses in which gene expression from two different promoters is determined in the same cell, tissue or organism; imaging, and FACS sorting of mixed cell populations.

In genetic reporting, examples that currently benefit from dual-reporter assays include individual cells or cell populations (such as cells dispersed in culture, segregated tissues, or whole animals) genetically or otherwise manipulated to simultaneously express, or contain, two or more different reporter proteins, in microorganisms and/or host plant or animal cells, etc. For example, the activity of one gene may report the impact of the specific experimental conditions, while the activity of the second reporter gene provides an internal control by which all sets of experimental values can be normalized.

Cell-free reconstituted systems that may benefit from dual-enzyme reporter technology are cellular lysates derived for the simultaneous translation, or coupled transcription and translation, of independent genetic materials encoding experimental and control reporter enzymes. Immunoassays may, likewise, be designed for dual-reporting of both experimental and control values from within a single sample. Preferred dual-reporter systems may be comprised of two enzyme assays with compatible chemistries, and identical temperature and handling conditions, speed, sensitivity, and instrumentation required for detection; or alternatively completely different chemistries and optima such that differential assay conditions can be used to validate another form of measurement such as imaging.

Modified Cells. The terms "engineered" and "genetically modified" cells are intended to refer to a cell into which an exogenous DNA segment or gene that includes a red-shifted luciferase gene sequence has been introduced. Such cells are distinguishable from naturally occurring cells that do not contain an introduced exogenous DNA segment, gene or combination. Established cell lines that grow continuously in culture from a single cell or group of cells may be used in connection with the present invention. Examples of such mammalian host cell lines include VERO cells, HeLa cells, Chinese hamster ovary (CHO) cell lines, COS cells, such as COS-7, W138, BHK, HepG2, 3T3, RIN, MDCK, A549, PC12, K562 and 293 cells. Such cell lines may also be derived from non-mammalian species.

Primary cell lines may also be used. Primary cell lines are those cells that have been removed from an animal or human subject and are capable of surviving in culture for a limited period of time. Such cells are often manipulated, e.g. to introduce a beneficial or deleterious gene, and then re-introduced into an animal similar to that from which they were originally obtained. This technique is often termed ex, vivo gene therapy. Primary cells of all organisms may be used in such studies. Such cells include, by way of example only, bone marrow cells, nerve cells, lung epithelial cells and hepatocytes. Cells that were not obtained from the ultimate host animal may be cells from an immunologically compatible animal, cells that have been immunologically modified or disabled, cells that are protected within a semi-permeable device in the host animal and even largely unmodified cells that are intended to have a temporary life span within the host animal.

In vivo analysis: Because of the red-shift, the luciferase of the present invention is particularly well-suited for in vivo applications where it is desirable to track cells for expression levels, position within an animal. The expression construct may be delivered to a higher organism (i.e. plants and animals) using a variety of techniques. Delivery may be made to somatic cells, e.g. in gene therapy applications, tumor cells (in vivo or in culture), or to the germline, e.g. in transgenic mice and other animals. Organisms of interest include mammals, e.g. primates, rodents, bovines, ovines, felines canines, etc., lower eukaryotes such as flies, worms, etc., plants, including monocots and dicots; microorganisms such as yeast, bacteria, protozoans, viruses and the like as known to those of skill in the art.

One approach is to transfect or transduce cells with DNA containing the gene of interest, e.g., by permeabilizing the cell membrane either chemically or physically or with viral mediated transfer. This approach is generally used with cells that can be temporarily removed from the body, e.g. lymphocytes, embryonic stem cells, etc. Calcium phosphate precipitation, DEAE-dextran, electroporation, and direct microinjection are examples of such methods. Alternatively, liposomes or protein conjugates formed with certain lipids and amphophilic peptides can be used for in vivo and in vitro transfection.

It is known that cells can take up naked DNA and express encoded proteins. Plasmids may be used to directly transfer genetic material into a cell, using DNA segments themselves as delivery agents. This technology for delivering DNA to tissues can be used for DNA-based therapeutics as in gene therapy or gene vaccines. Parenteral, mucosal and gene-gun inoculations (Fynan et al., 1993) may be used.

A variety of viral vectors may be used, e.g. herpes simplex virus (U.S. Pat. No. 5,288,641, incorporated herein by reference), cytomegalovirus, retroviruses, adenoviruses, adeno-assocaited viruses and the like. A wide variety of genes have been delivered via viral vectors. For example, herpes simplex-thymidine kinase (HS-tK) gene has been delivered to brain tumors using a retroviral vector system, where it successfully induced susceptibility to the antiviral agent ganciclovir. Gene delivery using second generation viral vectors has also been reported, e.g. with variants of the Moloney murine leukemia virus and lentiviruses. Other viral vectors include vaccinia virus; defective hepatitis B viruses; adenovirus and adeno-associated virus, which are engineered to serve as vectors for gene transfer.

Promoter analysis: A range of promoters can be tested for their suitability for use with a given gene, cell, or system, including in vitro uses, e.g. identifying a suitable promoter for use in recombinant expression, high level protein production, etc., and in vivo uses, e.g. pre-clinical testing, gene therapy in human subjects, etc.

For promoter analysis, the luciferase coding sequence is operably linked to the promoter to be tested. Alternatively, the gene can be introduced, without a promoter, into the chromosome with the intent of identifying a previously uncharacterized promoter element (the technique referred to as promoter trapping). The production of light is related to the expression levels of the luciferase, which are controlled by the promoter element. The results are generally compared to a control gene, cell or system. Promoters suitable for testing include tissue-specific promoters and inducible promoters. Testing of tissue-specific promoters allows preferred or optimal promoters for use with a given cell to be identified and distinguished from a range of possible promoters. Optimizing the combination of a given promoter and a given cell type in recombinant expression and protein production can often be necessary to ensure that the highest possible levels are achieved.

A further development of using promoters along with the luciferase of the present invention is its use in screening protocols. In these embodiments, which are generally conducted in vitro, a genetically engineered cell is used to identify the presence of a particular compound or agent in a composition. The luciferase gene is positioned downstream of a promoter that is known to be inducible by the agent that one wishes to identify. Expression of luciferase in the cells will normally be silent, and will be switched on by exposing the cell to a composition that contains the selected agent. In using a promoter that is responsive to, for example, a heavy metal, a toxin, a hormone, a cytokine or other defined molecule, the presence of a heavy metal, toxin, hormone, cytokine or such like can readily be determined. Alternatively, constitutive expression of the reporter by genetically engineered cells can be useful in determining repressors of particular promoters.

Kits and markers: In methods to produce bioluminescent molecular weight markers, a red-shifted luciferase gene sequence is generally fused to one or more DNA sequences that encode proteins having defined amino acid sequences and the fusion proteins are expressed from an expression vector. Expression results in the production of bioluminescent proteins of defined molecular weight or weights that may be used as markers. Preferably, purified bioluminescent proteins would be subjected to size-fractionation, such as by using a gel. A determination of the molecular weight of an unknown protein is then made by compiling a calibration curve from the bioluminescent standards and reading the unknown molecular weight from the curve.

Expression kits comprising red-shifted luciferase genes may be provided. Such kits will generally contain a formulation of a red-shifted luciferase gene or a vector capable of expressing a red-shifted luciferase gene. The gene or vector may be provided in a pharmaceutically acceptable formulation. A second bioluminescent gene or vector construct may also be provided. The vector(s) will be provided in a suitable formulation or as a lyophilized powder, and the kits may also comprise, or be packaged with, one or more further molecular biological reagents, such as restriction enzymes, and with instructions for use.

The following examples are put forth so as to provide those of ordinary skill in the art with a complete disclosure and description of how to make soluble proteins and carry out the methodology for finding such proteins, and are not intended to limit the scope of what is regarded as the invention. Efforts have been made to insure accuracy with respect to the numbers used (e.g. amounts, temperature, concentrations, etc.) but some experimental errors and deviations should be accounted for. Unless otherwise indicated, parts are parts by weight, molecular weight is weight average molecular weight, temperature is in degrees centigrade; and pressure is at or near atmospheric.

EXPERIMENTAL

EXAMPLE 1
Production of a Red-Shifted Luciferase

Noninvasive imaging of gene expression in vivo using the luciferase reporter can be enhanced by increasing both the light intensity (numbers of photons) emitted during the enzyme reaction and/or by shifting the wavelength of the emitted photons to a longer, more penetrating wavelength (e.g. from yellow-green to red). In addition, luciferases that emit at different wavelengths permit multicolor assays. Red light has a greater ability to penetrate the relatively opaque tissues of mammals than blue or yellow light. Mutagenesis was used to convert the yellow-green luciferase to emit in the red range (>600 nm) by site-directed mutagenesis.

Mutagenesis: Using PCR-based site-directed mutagenesis, mutations were introduced at positions that may shift the yellow-green emission to red. The sites targeted for mutagenesis were Gly 324 and Val 323. Mutations were confirmed by restriction analysis, selected clones were transfected into NIH 3T3 cells, and expression levels in living cells were evaluated using an intensified CCD camera (blue sensitive with sensitivity at $\geq 600$ nm) and a cooled intensified CCD camera (blue to red sensitive with sensitivity at $\leq 850$ nm).

Spectral analysis. Emission spectra from lysates of transfected cells showing the most intense signals were determined using a standard luciferase assay (Promega Corp.) on a Hitachi F-4010 fluorescence spectrophotometer with the excitation source turned off. Compared to wild-type, all mutant luciferases demonstrated red-orange emission with variability in signal intensity. Two emission peaks were detected in each spectrum, each clone with different relative peak heights at 560 nm (yellow-green, wild-type) and 610 nm (red, mutant). A single clone, plasmid pGL3R, demonstrated a strong 610 nm peak with a minimum shoulder at 560 nm.

Sequence analysis. Sequence analyses of the complete luciferase coding regions of pGL3R and other clones confirmed the presence of the target mutations, although sequence variation was observed at several sites, likely resulting from the infidelity of Taq polymerase. The presence of second-site mutations in all clones tested suggested that they were compensatory changes, and differences among the clones in nature and position of amino acid substitutions provide a basis for the variability in spectra. The positions of these mutated sites were localized on the 3D structure of the North American firefly luciferase. Of the two compensatory mutations in the selected clone, $luc^{610}$, one was in close proximity to the active site, the putative substrate binding surface. Here, a polar residue (Thr) was substituted for a small hydrophobic residue (Ala, position 452).

Results

To generate red-emitting bioluminescent reporters, mutations were introduced into an optimized firefly luciferase coding sequence (pGL3, Promega Corp). Codons were targeted for mutation based on mutational and translational studies of beetle luciferases. The template for these PCR introduced mutations was the modified version of the wild-type North American firefly luciferase gene (present on the plasmid, pGL3). The previous modifications made by the manufacturer included removal of the peroxisome targeting site creating a more highly expressed cytoplasmic protein and replacement of insect preferred codons with those that are favored by mammalian cells (i.e. optimized mammalian codon usage). The manufacture's modifications result in higher expression in some mammalian cells.

Mutations were introduced by amplifying (via PCR) the luciferase coding sequence in two parts using primers that incorporated the mutations. The two halves were then mixed and reamplified with outer primers that were positioned at the termini of the coding region. This fragment was then ligated back into the original vector, pGL3, in its original context. The inferred locations of the altered amino acids in the 3D structure of luciferase reside on the face of the large globular domain of the enzyme in the putative substrate binding site (FIG. 1A). The target alteration sites are Gly 324, Val 323.

Figure 1B:
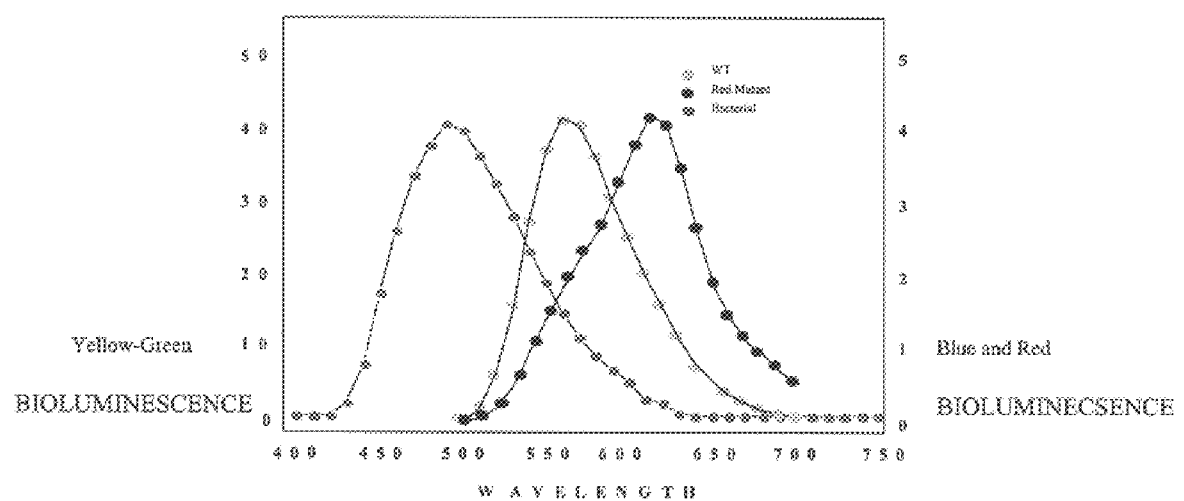
FIG. 1B is a spectral analysis of the mutated luciferase, compared to the wildtype enzyme and a bacterial luciferase.

These mutations result in a orange-red phenotype as determined by performing spectral analyses on lysates of NIH 3T3 cells transfected with plasmids containing the wild type and mutated luciferases (FIG. 1B). The bacterial enzyme from *Photorhabdus luminescens* has a spectral peak at 490 nm, the wildtype *P. pyralis* firefly enzyme at 560 nm and mutant of the *P. pyralis* firefly enzyme at 610 nm. The result of introducing the mutations was an enzyme whose photon emission was shifted from 560 nm (yellow-green) to 610 nm (orange-red).

The luciferase coding sequence in those plasmids that resulted in a spectral shift (to the red) was sequenced to confirm the presence of mutated codons. Each luciferase gene with a red shifted phenotype contained the introduced mutations, however the sequences contained additional substitutions, most likely introduced during PCR by the "error-prone" Taq polymerase. Some of the nucleotide differences were nonsynonymous; however, no two amino acid differences were shared among the red-shifted mutants, other than those that were intentionally introduced. The additional sequence changes likely account for subtle differences in the spectral emission in that some clones demonstrated shoulders, of varying intensities, at 560 nm (wavelength of the wildtype peak). This shoulder is apparent in the spectral analyses of the red mutant in FIG. 1; shown in this figure is the profile of a red-shifted mutant with the least intense 560 nm shoulder.

Red light transmits through tissues to a greater extent than do shorter wavelengths of light (blue and green). Thus, modified luciferases with long wavelengths (700 nm would be optimal due to a nearly complete lack of absorption of this wavelength by mammalian tissues) may likely improve sensitivity of detection from cells in tissues of living mammals and other organisms whose tissues absorb light of shorter wavelengths. The red mutant that was generated in these studies is used to monitor host gene expression, such that the increased penetration will permit localization of smaller numbers of tagged cells, or from cells with weakly expressed reporter genes. Red-emitting luciferases have utility, as greater sensitivity of detection is required and the field moves into 3D reconstructions of biological processes in living animals. To monitor gene expression in vivo, transgenic mice can be made with this red-shifted enzyme, since monitoring host response will likely require maximum sensitivity. Moreover, luciferases with similar protein sequences. and biochemical characteristics that emit at different wavelengths permit the development of dual color assays for monitoring multiple parameters in live animals. The similarity of these luciferases will be useful in normalizing for reporter activity.

EXAMPLE 2

Two Color Assay to Simultaneously Monitor Infection and Host Response

A noninvasive two-color assay was utilized for simultaneously detecting pathogens and monitoring host response. A mouse-virulent Salmonella strain labeled by luciferase expression (SL1344/ ux), was used to infect a susceptible model transgenic "indicator" mouse line. This indicator Tg mouse line contained a transgene consisting of the regulatory region of the HIV LTR fused to the coding region of firefly luciferase (LTR-luc), as a surrogate marker for immune cell activation or recruitment (FIG. 2).

Figure 2:
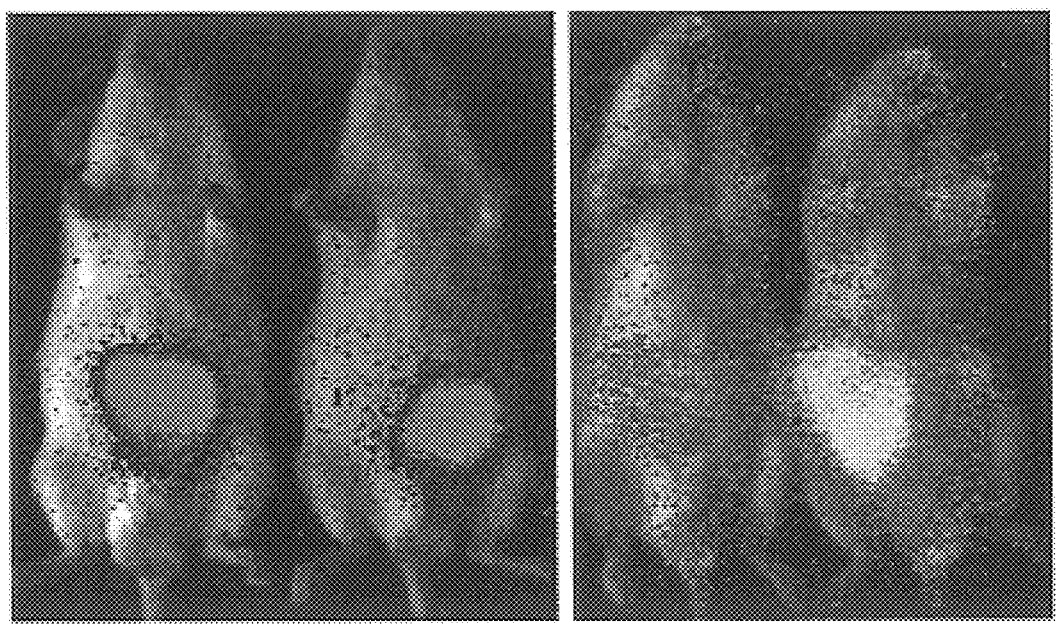
FIG. 2 shows a two-color assay for bacterial infection and host response in living animals.

FIG. 2: Salmonella emitting blue light (489 nm) were used to infect two mice (LEFT), and LTR-luc mice that emit yellow-green light (560 nm) were infected with nonbioluminescent Salmonella (RIGHT). Color scales on the pseudocolor images were set to represent approximate colors of luciferase emission for each image. Salmonella bioluminescence localizes to the cecum and activation of LTR-luc was observed in a similar region in infected tissues. LTR-luc expression was also observed in the paws and nose of these animals but this was also observed in uninfected mice.

The bacterial and insect luciferases in this study are biologically distinct, and emit different colors of light; blue (489 nm) and yellow-green (560 nm), respectively. Four week old LTR-luc mice were either infected orally with SL1344 (without the lux operon), SL1344lux, or were not infected, and were imaged over a 7 d period. Animals infected with non-bioluminescent Salmonella exhibited high levels of photon emission over the abdominal region compared with uninfected animals indicating immune recruitment or activation. Animals infected with bioluminescent Salmonella were also brightly bioluminescent and short and long pass filters were used to attempt to select specific wavelengths of emission from lux and luc, respectively, allowing distinction between the pathogen and host gene expression. This experiment demonstrated that real-time, simultaneous analyses of the course of bacterial infection and the host response in intact living animals may be possible and that previously unavailable information may be obtained. This type of assay will accelerate studies aimed at dissecting the complex interwoven pathways of pathogenesis.

Infection of transgenic mice, where the transgene consists of the regulatory region of the HIV-1 LTR driving the expression of luciferase, with wildtype Salmonella (a strain, SL1344, not engineered to express luciferase) resulted in increased bioluminescence in the colon, a primary site of Salmonella colonization (FIG. 2). This result indicated that either there was a recruitment of immune cells expressing luciferase or an activation of luciferase-expressing resident cells of the GI tract, the primary site of bacterial colonization. This could be due to direct effect of bacterial lipopolysaccharide (LPS) on these cells or to the expression of cytokines that are known to increase expression from the HIV-1 LTR (IFN$_\gamma$ or IL-2).

Figure 3:
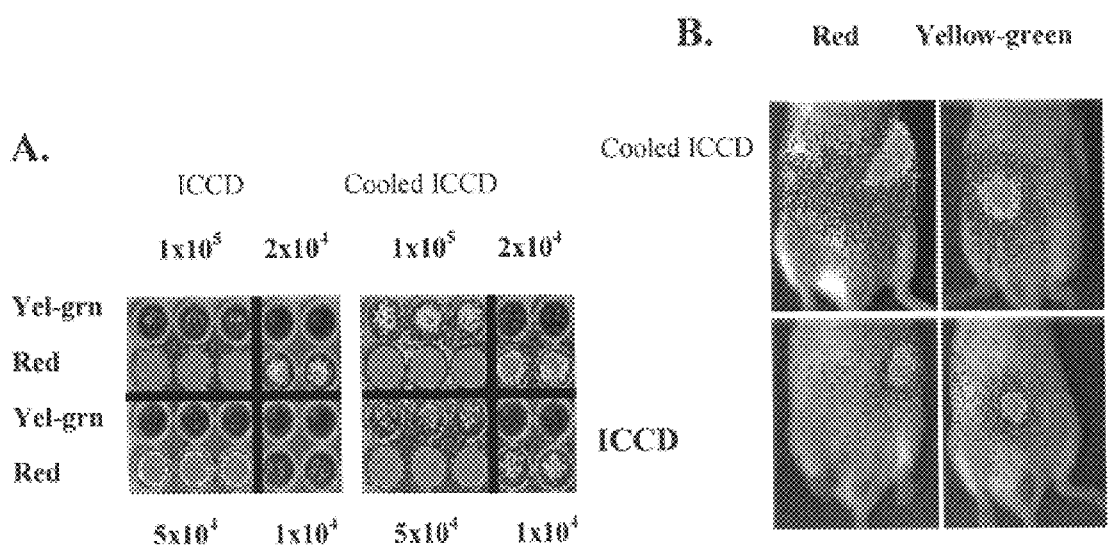
FIG. 3 is a comparison of the red shifted mutant to the wild type luciferase in cultured cells (A), and in living mice (B) using two different intensified CCD cameras.

FIG. 3 shows cells (NIH 3T3) expressing either the luc$^{560}$ (yel-grn) or luc$^{610}$ (red), imaged twice in culture and. twice in animals; once with an intensified CCD camera (Hamamatsu C2400–32) and once with a cooled intensified CCD camera. The numbers of cells in each quadrant of panel A are given. These data demonstrated that the cells with the red mutant were more intense per cell, and that the ICCD camera was more sensitive at detecting both wavelengths of emission. Panel B demonstrates that when cell populations, matched for light intensity, were injected into animals, the red light was transmitted to a greater extent, $3.6 \times 10^5$ photons compared to $2.6 \times 10^5$ photons for the yellow green emitter (compare left to right panels). This difference could not be detected with the ICCD camera, only with the cooled intensified camera. In addition, when the same animals were analyzed by the two cameras, the cooled camera was more sensitive at detecting both colors of light; $3.6 \times 10^5$ photons vs. $2.9 \times 10^4$ photons for red and $2.6 \times 10^5$ photons vs. $3.0 \times 10^4$ photons for the yellow-green (compare upper images to lower).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated nucleic acid other than an intact chromosome encoding a red-shifted *Photinus pyralis* luciferase that emits a primary peak of light at 610 nm.

2. An isolated nucleic acid other than an intact chromosome encoding a red-shifted *Photinus pyralis* luciferase comprising amino acid substitutions as compared to a wild-type luciferase at the position corresponding to positions 323 and 324 in SEQ ID NO:4.

3. An isolated nucleic acid other than an intact chromosome encoding a red-shifted *Photinus pyralis* luciferase comprising the amino acid substitutions V323I and G324S as set forth in SEQ ID NO:4.

4. The nucleic acid of claim 2, wherein said red-shifted *Photinus pyralis* luciferase emits a primary peak of light at 610 nm.

5. The nucleic acid of claim 4, wherein said red-shifted *Photinus pyralis* luciferase comprises an amino acid substitution at position 452.

6. The nucleic acid of claim 5, wherein said red-shifted *Photinus pyralis* comprises a polar amino acid at position 452.

7. The nucleic acid of claim 6 wherein said amino acid substitution is A452T.

8. A first expression vector comprising a first reporter gene operably linked to a promoter, wherein said first reporter gene comprises the nucleic acid according to claim 1.

9. A cell comprising an expression vector according to claim 8.

10. A cell according to claim 9, wherein said cell is a mammalian cell.

11. A method for producing red-shifted luciferase, said method comprising:
growing a cell according to claim 9, whereby said red-shifted luciferase is expressed, and isolating said red-shifted luciferase free of other proteins.

12. A method for detecting the presence of a red-shifted luciferase in a cell, the method comprising:
introducing the expression vector of claim 8 into said cell;
contacting said cell with a luciferase substrate; and
detecting the presence of light emitted at 610 nm.

13. The method of claim 12, further comprising:
detecting the presence of a second reporter gene.

14. The method of claim 13, wherein said second reporter gene is present on said expression vector.

15. The method of claim 13, wherein said second reporter gene is present on a second expression vector.

16. The method of claim 13, wherein said second reporter gene encodes a luminescent protein.

17. The method of claim 16, wherein said second reporter gene encodes a green fluorescent protein.

18. The method of claim 16, wherein said second reporter gene encodes a fluorescent protein emitting at a peak other than in the green part of the spectrum.

19. The method according to claim 16, wherein said luminescent protein is a luciferase emitting at a peak other than 610 nm.

20. A first expression vector comprising a first reporter gene operably linked to a promoter, wherein said first reporter gene comprises the nucleic acid according to claim 2.

21. A cell comprising an expression vector according to claim 20.

22. A cell according to claim 21, wherein said cell is a mammalian cell.

23. A method for detecting the presence of a red-shifted luciferase in a cell, the method comprising:

introducing the expression vector of claim 20 into said cell;

contacting said cell with a luciferase substrate; and detecting the presence of light emitted at 610 nm.

24. The method of claim 23, further comprising:

detecting the presence of a second reporter gene, wherein said second reporter gene is present on said expression vector.

25. The method of claim 24, wherein said second reporter gene is present on a second expression vector.

26. The method of claim 24, wherein said second reporter gene encodes a luminescent protein.

27. An isolated nucleic acid other than an intact chromosome encoding a red-shifted Photinus pyralis luciferase as set forth in SEQ ID NO:4 and further comprising amino acids substitutions that are conservative with respect to isoleucine at position 323 and conservative with respect to serine at position 324.

* * * * *

SEQUENCE LISTING

<160> NUMBER OF SEQ ID NOS: 12

<210> SEQ ID NO 1
<211> LENGTH: 1686
<212> TYPE: DNA

<213> ORGANISM: Artificial Sequence
<220> FEATURE:
<223> OTHER INFORMATION: Red shifted luciferase mutation
<221> NAME/KEY: CDS
<222> LOCATION: (1)...(1650)

<400> SEQUENCE: 1

```
atg gaa gac gcc aaa aac ata aag aaa ggc ccg gcg cca ttc tat ccg      48
Met Glu Asp Ala Lys Asn Ile Lys Lys Gly Pro Ala Pro Phe Tyr Pro
 1               5                  10                  15 ctg gaa gat gga acc gct gga gag caa ctg cat aag gct atg aag aga      96
Leu Glu Asp Gly Thr Ala Gly Glu Gln Leu His Lys Ala Met Lys Arg
             20                  25                  30 tac gcc ctg gtt cct gga aca att gct ttt aca gat gca cat atc gag     144
Tyr Ala Leu Val Pro Gly Thr Ile Ala Phe Thr Asp Ala His Ile Glu
         35                  40                  45 gtg gac atc act tac gct gag tac ttc gaa atg tcc gtt cgg ttg gca     192
Val Asp Ile Thr Tyr Ala Glu Tyr Phe Glu Met Ser Val Arg Leu Ala
     50                  55                  60 gaa gct atg aaa cga tat ggg ctg aat aca aat cac aga atc gtc gta     240
Glu Ala Met Lys Arg Tyr Gly Leu Asn Thr Asn His Arg Ile Val Val
 65                  70                  75                  80 tgc agt gaa aac tct ctt caa ttc ttt atg ccg gtg ttg ggc gcg tta     288
Cys Ser Glu Asn Ser Leu Gln Phe Phe Met Pro Val Leu Gly Ala Leu
                 85                  90                  95 ttt atc gga gtt gca gtt gcg ccc gcg aac gac att tat aat gaa cgt     336
Phe Ile Gly Val Ala Val Ala Pro Ala Asn Asp Ile Tyr Asn Glu Arg
            100                 105                 110 gaa ttg ctc aac agt atg ggc att tcg cag cct acc gtg gtg ttc gtt     384
Glu Leu Leu Asn Ser Met Gly Ile Ser Gln Pro Thr Val Val Phe Val
        115                 120                 125 tcc aaa aag ggg ttg caa aaa att ttg aac gtg caa aaa aag ctc cca     432
Ser Lys Lys Gly Leu Gln Lys Ile Leu Asn Val Gln Lys Lys Leu Pro
    130                 135                 140 atc atc caa aaa att att atc atg gat tct aaa acg gat tac cag gga     480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt     528
Phe Gln Ser Met Tyr Thr Phe Val Thr Ser His Leu Pro Pro Gly Phe
                165                 170                 175 aat gaa tac gat ttt gtg cca gag tcc ttc gat agg gac aag aca att     576
Asn Glu Tyr Asp Phe Val Pro Glu Ser Phe Asp Arg Asp Lys Thr Ile
            180                 185                 190 gca ctg atc atg aac tcc tct gga tct act ggt ctg cct aaa ggt gtc     624
Ala Leu Ile Met Asn Ser Ser Gly Ser Thr Gly Leu Pro Lys Gly Val
        195                 200                 205 gct ctg cct cat aga act gcc tgc gtg aga ttc tcg cat gcc aga gat     672
Ala Leu Pro His Arg Thr Ala Cys Val Arg Phe Ser His Ala Arg Asp
    210                 215                 220 cct att ttt ggc aat caa atc att ccg gat act gcg att tta agt gtt     720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg     768
Val Pro Phe His His Gly Phe Gly Met Phe Thr Thr Leu Gly Tyr Leu
                245                 250                 255 ata tgt gga ttt cga gtc gtc tta atg tat aga ttt gaa gaa gag ctg     816
Ile Cys Gly Phe Arg Val Val Leu Met Tyr Arg Phe Glu Glu Glu Leu
            260                 265                 270 ttt ctg agg agc ctt cag gat tac aag act caa agt gcg ctg ctg gtg     864
Phe Leu Arg Ser Leu Gln Asp Tyr Lys Thr Gln Ser Ala Leu Leu Val
        275                 280                 285
```

-continued

```
cca acc cta ttc tcc ttc ttc gcc aaa agc act ctg att gac aaa tac     912
Pro Thr Leu Phe Ser Phe Phe Ala Lys Ser Thr Leu Ile Asp Lys Tyr
    290                 295                 300 gat tta tct aat tta cac gaa att gct tct ggt ggc gct cca ctc tct     960
Asp Leu Ser Asn Leu His Glu Ile Ala Ser Gly Gly Ala Pro Leu Ser
305                 310                 315                 320 aag gaa atc agc gaa gcg gtt gcc aag agg ttc cat ctg cca ggt atc    1008
Lys Glu Ile Ser Glu Ala Val Ala Lys Arg Phe His Leu Pro Gly Ile
                325                 330                 335 agg caa gga tat ggg ctc act gag act aca tcg gct att ctg att aca    1056
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt    1104
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt    1152
Phe Glu Ala Lys Val Val Asp Leu Asp Thr Gly Lys Thr Leu Gly Val
    370                 375                 380 aat caa aga ggc gaa ctg tgt gtg aga ggt cct atg att atg tcc ggt    1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga    1248
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc    1296
Trp Leu His Ser Gly Asp Ile Ala Tyr Trp Asp Glu Asp Glu His Phe
            420                 425                 430 ttc atc gtt gac cgc ctg aag tct ctg att aag tac aaa ggc tat cag    1344
Phe Ile Val Asp Arg Leu Lys Ser Leu Ile Lys Tyr Lys Gly Tyr Gln
        435                 440                 445 gtg gct ccc act gaa ttg gaa tcc atc ttg ctc caa cac ccc aac atc    1392
Val Ala Pro Thr Glu Leu Glu Ser Ile Leu Leu Gln His Pro Asn Ile
    450                 455                 460 ttc gac gca ggt gtc gca ggt ctt ccc gac gat gac gcc ggt gaa ctt    1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa    1488
Pro Ala Ala Val Val Val Leu Glu His Gly Lys Thr Met Thr Glu Lys
                485                 490                 495 gag atc gcg gat tac gtc gcc agt caa gta aca acc gcg aaa aag ttg    1536
Glu Ile Ala Asp Tyr Val Ala Ser Gln Val Thr Thr Ala Lys Lys Leu
            500                 505                 510 cgc gga gga gtt gtg ttt gtg gac gaa gta ccg aaa ggt ctt acc gga    1584
Arg Gly Gly Val Val Phe Val Asp Glu Val Pro Lys Gly Leu Thr Gly
        515                 520                 525 aaa ctc gac gca aga aaa atc aga gag atc ctc ata aag gcc aag aag    1632
Lys Leu Asp Ala Arg Lys Ile Arg Glu Ile Leu Ile Lys Ala Lys Lys
    530                 535                 540 ggc gga aag atc gcc gtg taattctaga gtcggggcgg ccggccgctt           1680
Gly Gly Lys Ile Ala Val
545                 550 cgagca                                                             1686
```

<210> SEQ ID NO 2
<211> LENGTH: 550
<212> TYPE: PRT
<213> ORGANISM: Artificial Sequence
<220> FEATURE:
<223> OTHER INFORMATION: Red shifted luciferase mutation -continued

<400> SEQUENCE: 2

```
Met Glu Asp Ala Lys Asn Ile Lys Lys Gly Pro Ala Pro Phe Tyr Pro
 1               5                  10                  15
Leu Glu Asp Gly Thr Ala Gly Glu Gln Leu His Lys Ala Met Lys Arg
                20                  25                  30
Tyr Ala Leu Val Pro Gly Thr Ile Ala Phe Thr Asp Ala His Ile Glu
            35                  40                  45
Val Asp Ile Thr Tyr Ala Glu Tyr Phe Glu Met Ser Val Arg Leu Ala
 50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Gly Ile Ser Gln Pro Thr Val Val Phe Val
            115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
            195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Thr Gln Ser Ala Leu Leu Val
            275                 280                 285
Pro Thr Leu Phe Ser Phe Phe Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Ile Ser Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
```

```
Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
            435                 440                 445

Val Ala Pro Thr Glu Leu Glu Ser Ile Leu Leu Gln His Pro Asn Ile
            450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Ala Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
        530                 535                 540

Gly Gly Lys Ile Ala Val
545                 550

<210> SEQ ID NO 3
<211> LENGTH: 1686
<212> TYPE: DNA
<213> ORGANISM: Artificial Sequence
<220> FEATURE:
<223> OTHER INFORMATION: red-shifted luciferase mutation
<221> NAME/KEY: CDS
<222> LOCATION: (1)...(1650)
<223> OTHER INFORMATION: Coding sequence of Clone 1

<400> SEQUENCE: 3 atg gaa gac gcc aaa aac ata aag aaa ggc ccg gcg cca ttc tat ccg     48
Met Glu Asp Ala Lys Asn Ile Lys Lys Gly Pro Ala Pro Phe Tyr Pro
 1               5                   10                  15 ctg gaa gat gga acc gct gga gag caa ctg cat aag gct atg aag aga     96
Leu Glu Asp Gly Thr Ala Gly Glu Gln Leu His Lys Ala Met Lys Arg
            20                  25                  30 tac gcc ctg gtt cct gga aca att gct ttt aca gat gca cat atc gag    144
Tyr Ala Leu Val Pro Gly Thr Ile Ala Phe Thr Asp Ala His Ile Glu
        35                  40                  45 gtg gac atc act tac gct gag tac ttc gaa atg tcc gtt cgg ttg gca    192
Val Asp Ile Thr Tyr Ala Glu Tyr Phe Glu Met Ser Val Arg Leu Ala
    50                  55                  60 gaa gct atg aaa cga tat ggg ctg aat aca aat cac aga atc gtc gta    240
Glu Ala Met Lys Arg Tyr Gly Leu Asn Thr Asn His Arg Ile Val Val
65                  70                  75                  80 tgc agt gaa aac tct ctt caa ttc ttt atg ccg gtg ttg ggc gcg tta    288
Cys Ser Glu Asn Ser Leu Gln Phe Phe Met Pro Val Leu Gly Ala Leu
                85                  90                  95 ttt atc gga gtt gca gtt gcg ccc gcg aac gac att tat aat gaa cgt    336
Phe Ile Gly Val Ala Val Ala Pro Ala Asn Asp Ile Tyr Asn Glu Arg
            100                 105                 110 gaa ttg ctc aac agt atg ggc att tcg cag cct acc gtg gtg ttc gtt    384
Glu Leu Leu Asn Ser Met Gly Ile Ser Gln Pro Thr Val Val Phe Val
        115                 120                 125 tcc aaa aag ggg ttg caa aaa att ttg aac gtg caa aaa aag ctc cca    432
Ser Lys Lys Gly Leu Gln Lys Ile Leu Asn Val Gln Lys Lys Leu Pro
    130                 135                 140 atc atc caa aaa att att atc atg gat tct aaa acg gat tac cag gga    480
Ile Ile Gln Lys Ile Ile Ile Met Asp Ser Lys Thr Asp Tyr Gln Gly
```

```
                    145                 150                 155                 160
ttt cag tcg atg tac acg ttc gtc aca tct cat cta cct ccc ggt ttt      528
Phe Gln Ser Met Tyr Thr Phe Val Thr Ser His Leu Pro Pro Gly Phe
                165                 170                 175 aat gaa tac gat ttt gtg cca gag tcc ttc gat agg gac aag aca att      576
Asn Glu Tyr Asp Phe Val Pro Glu Ser Phe Asp Arg Asp Lys Thr Ile
            180                 185                 190 gca ctg atc atg aac tcc tct gga tct act ggt ctg cct aaa ggt gtc      624
Ala Leu Ile Met Asn Ser Ser Gly Ser Thr Gly Leu Pro Lys Gly Val
        195                 200                 205 gct ctg cct cat aga act gcc tgc gtg aga ttc tcg cat gcc aga gat      672
Ala Leu Pro His Arg Thr Ala Cys Val Arg Phe Ser His Ala Arg Asp
    210                 215                 220 cct att ttt ggc aat caa atc att ccg gat act gcg att tta agt gtt      720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg      768
Val Pro Phe His His Gly Phe Gly Met Phe Thr Thr Leu Gly Tyr Leu
                245                 250                 255 ata tgt gga ttt cga gtc gtc tta atg tat aga ttt gaa gaa gag ctg      816
Ile Cys Gly Phe Arg Val Val Leu Met Tyr Arg Phe Glu Glu Glu Leu
            260                 265                 270 ttt ctg agg agc ctt cag gat tac aag att caa agt gcg ctg ctg gtg      864
Phe Leu Arg Ser Leu Gln Asp Tyr Lys Ile Gln Ser Ala Leu Leu Val
        275                 280                 285 cca acc cta ttc tcc ttc ttc gcc aaa agc act ctg att gac aaa tac      912
Pro Thr Leu Phe Ser Phe Phe Ala Lys Ser Thr Leu Ile Asp Lys Tyr
    290                 295                 300 gat tta tct aat tta cac gaa att gct tct ggt ggc gct cca ctc tct      960
Asp Leu Ser Asn Leu His Glu Ile Ala Ser Gly Gly Ala Pro Leu Ser
305                 310                 315                 320 aag gaa atc agc gaa gcg gtt gcc aag agg ttc cat ctg cca ggt atc     1008
Lys Glu Ile Ser Glu Ala Val Ala Lys Arg Phe His Leu Pro Gly Ile
                325                 330                 335 agg caa gga tat ggg ctc act gag act aca tca gct att ctg att aca     1056
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt     1104
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt     1152
Phe Glu Ala Lys Val Val Asp Leu Asp Thr Gly Lys Thr Leu Gly Val
    370                 375                 380 aat caa aga ggc gaa ctg tgt gtg aga ggt cct atg att atg tcc ggt     1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga     1248
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc     1296
Trp Leu His Ser Gly Asp Ile Ala Tyr Trp Asp Glu Asp Glu His Phe
            420                 425                 430 ttc gtc gtt gac cgc ctg aag tct ctg att aag tac aaa ggc tat cag     1344
Phe Val Val Asp Arg Leu Lys Ser Leu Ile Lys Tyr Lys Gly Tyr Gln
        435                 440                 445 gtg gct ccc gct gaa ttg gaa tcc atc ttg ctc caa cac ccc aac atc     1392
Val Ala Pro Ala Glu Leu Glu Ser Ile Leu Leu Gln His Pro Asn Ile
    450                 455                 460 ttc gac gca ggt gtc gca ggt ctt ccc gac gat gac gcc ggt gaa ctt     1440
```

-continued

```
Phe Asp Ala Gly Val Ala Gly Leu Pro Asp Asp Ala Gly Glu Leu
465                 470                 475                 480 ccc gcc gcc gtt gtt gtt ttg gag cac gga aag acg atg acg gaa aaa          1488
Pro Ala Ala Val Val Val Leu Glu His Gly Lys Thr Met Thr Glu Lys
                    485                 490                 495 gag atc gtg gat tac gtc gcc agt caa gta aca acc gcg aaa aag ttg          1536
Glu Ile Val Asp Tyr Val Ala Ser Gln Val Thr Thr Ala Lys Lys Leu
                500                 505                 510 cgc gga gga gtt gtg ttt gtg gac gaa gta ccg aaa ggt ctt acc gga          1584
Arg Gly Gly Val Val Phe Val Asp Glu Val Pro Lys Gly Leu Thr Gly
            515                 520                 525 aaa ctc gac gca aga aaa atc aga gag atc ctc ata aag gcc aag aag          1632
Lys Leu Asp Ala Arg Lys Ile Arg Glu Ile Leu Ile Lys Ala Lys Lys
        530                 535                 540 ggc gga aag atc gcc gtg taattctaga gtcggggcgg ccggccgctt                 1680
Gly Gly Lys Ile Ala Val
545                 550 cgagca                                                                   1686
```

<210> SEQ ID NO 4
<211> LENGTH: 550
<212> TYPE: PRT
<213> ORGANISM: Artificial Sequence
<220> FEATURE:
<223> OTHER INFORMATION: Red shifted luciferase mutation

<400> SEQUENCE: 4

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240
```

```
Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Ile Ser Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Val Val Asp Arg Leu Lys Ser Leu Ile Lys Tyr Lys Gly Tyr Gln
    435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550

<210> SEQ ID NO 5
<211> LENGTH: 1685
<212> TYPE: DNA
<213> ORGANISM: Artificial Sequence
<220> FEATURE:
<223> OTHER INFORMATION: red-shifted luciferase mutation
<221> NAME/KEY: CDS
<222> LOCATION: (1)...(1650)
<221> NAME/KEY: misc_feature
<222> LOCATION: (1)...(1685)
<223> OTHER INFORMATION: n = A,T,C or G

<400> SEQUENCE: 5 nnn nnn nnn nnn nnn nac ata aag aaa ggc ccg gcg cca ttc tat ccg    48
Xaa Xaa Xaa Xaa Xaa Xaa Ile Lys Lys Gly Pro Ala Pro Phe Tyr Pro
  1               5                  10                  15
```

```
ctg gaa gat gga acc gct gga gag caa ctg cat aag gct atg aag aga    96
Leu Glu Asp Gly Thr Ala Gly Glu Gln Leu His Lys Ala Met Lys Arg
         20                  25                  30 tac gcc ctg gtt cct gga aca att gct ttt aca gat gca cat atc gag   144
Tyr Ala Leu Val Pro Gly Thr Ile Ala Phe Thr Asp Ala His Ile Glu
     35                  40                  45 gtg gac atc act tac gct gag tac ttc gaa atg tcc gtt cgg ttg gca   192
Val Asp Ile Thr Tyr Ala Glu Tyr Phe Glu Met Ser Val Arg Leu Ala
 50                  55                  60 gaa gct atg aaa cga tat ggg ctg aat aca aat cac aga atc gtc gta   240
Glu Ala Met Lys Arg Tyr Gly Leu Asn Thr Asn His Arg Ile Val Val
 65                  70                  75                  80 tgc agt gaa aac tct ctt caa ttc ttt atg ccg gtg ttg ggc gcg tta   288
Cys Ser Glu Asn Ser Leu Gln Phe Phe Met Pro Val Leu Gly Ala Leu
                 85                  90                  95 ttt atc gga gtt gca gtt gcg ccc gcg aac gac att tat aat gaa cgt   336
Phe Ile Gly Val Ala Val Ala Pro Ala Asn Asp Ile Tyr Asn Glu Arg
             100                 105                 110 gaa ttg ctc aac agt atg ggc att tcg cag cct acc gtg gtg ttc gtt   384
Glu Leu Leu Asn Ser Met Gly Ile Ser Gln Pro Thr Val Val Phe Val
         115                 120                 125 tcc aaa aag ggg ttg caa aaa att ttg aac gtg caa aaa aag ctc cca   432
Ser Lys Lys Gly Leu Gln Lys Ile Leu Asn Val Gln Lys Lys Leu Pro
     130                 135                 140 atc atc caa aaa att att atc atg gat tct aaa acg gat tac cag gga   480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt   528
Phe Gln Ser Met Tyr Thr Phe Val Thr Ser His Leu Pro Pro Gly Phe
                 165                 170                 175 aat gaa tac gat ttt gtg cca gag tcc ttc gat agg gac aag aca att   576
Asn Glu Tyr Asp Phe Val Pro Glu Ser Phe Asp Arg Asp Lys Thr Ile
             180                 185                 190 gca ctg atc atg aac tcc tct gga tct act ggt ctg cct aaa ggt gtc   624
Ala Leu Ile Met Asn Ser Ser Gly Ser Thr Gly Leu Pro Lys Gly Val
         195                 200                 205 gct ctg cct cat aga act gcc tgc gtg aga ttc tcg cat gcc aga gat   672
Ala Leu Pro His Arg Thr Ala Cys Val Arg Phe Ser His Ala Arg Asp
     210                 215                 220 cct att ttt ggc aat caa atc att ccg gat act gcg att tta agt gtt   720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg   768
Val Pro Phe His His Gly Phe Gly Met Phe Thr Thr Leu Gly Tyr Leu
                 245                 250                 255 atg tgt gga ttt cga gtc gtc tta atg tat aga ttt gaa gaa gag ctg   816
Met Cys Gly Phe Arg Val Val Leu Met Tyr Arg Phe Glu Glu Glu Leu
             260                 265                 270 ttt ctg agg agc ctt cag gat tac aag att caa agt gcg ctg ctg gtg   864
Phe Leu Arg Ser Leu Gln Asp Tyr Lys Ile Gln Ser Ala Leu Leu Val
         275                 280                 285 cca acc cta ttc tcc ttc ttc gct aaa agc act ctg att gac aaa tac   912
Pro Thr Leu Phe Ser Phe Phe Ala Lys Ser Thr Leu Ile Asp Lys Tyr
     290                 295                 300 gat tta tct aat tta cac gaa att gct tcg ggt ggc gct cca ctc tct   960
Asp Leu Ser Asn Leu His Glu Ile Ala Ser Gly Gly Ala Pro Leu Ser
305                 310                 315                 320 aag gaa atc agc gaa gcg gtt gcc aag agg ttc cat ctg cca ggt atc  1008
Lys Glu Ile Ser Glu Ala Val Ala Lys Arg Phe His Leu Pro Gly Ile
```

-continued

```
                325                 330                 335
agg caa gga tat ggg ctc act gag act aca tca gct att ctg att aca    1056
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt    1104
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt    1152
Phe Glu Ala Lys Val Val Asp Leu Asp Thr Gly Lys Thr Leu Gly Val
    370                 375                 380 aat caa aga ggc gaa ctg tgt gtg aga ggt cct atg att atg tcc ggt    1200
Asn Gln Arg Gly Glu Leu Cys Val Arg Gly Pro Met Ile Met Ser Gly
385                 390                 395                 400 tat gta agc aat ccg gaa gcg acc aac gcc ttg att gac aag gat gga    1248
Tyr Val Ser Asn Pro Glu Ala Thr Asn Ala Leu Ile Asp Lys Asp Gly
                405                 410                 415 tgg cta cat tct gga gac ata gct tac tgg gac gaa gac gaa cac ttc    1296
Trp Leu His Ser Gly Asp Ile Ala Tyr Trp Asp Glu Asp Glu His Phe
            420                 425                 430 ttc atc gtt gac cgc ctg aag tct ctg att aag tac aaa ggc tat cag    1344
Phe Ile Val Asp Arg Leu Lys Ser Leu Ile Lys Tyr Lys Gly Tyr Gln
        435                 440                 445 gtg gct ccc gct gaa ttg gaa tcc atc ttg ctc caa cac ccc aac atc    1392
Val Ala Pro Ala Glu Leu Glu Ser Ile Leu Leu Gln His Pro Asn Ile
    450                 455                 460 ttc gac gca ggt gtc gca ggt ctt ccc gac gat gac gcc ggt gaa ctt    1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa    1488
Pro Ala Ala Val Val Val Leu Glu His Gly Lys Thr Met Thr Glu Lys
                485                 490                 495 gag atc gtg gat tac gtc gcc agt caa gta aca acc gcg aaa aag ttg    1536
Glu Ile Val Asp Tyr Val Ala Ser Gln Val Thr Thr Ala Lys Lys Leu
            500                 505                 510 cgc gga gga gtt gtg ttt gtg gac gaa gta ccg aaa ggt ctt acc gga    1584
Arg Gly Gly Val Val Phe Val Asp Glu Val Pro Lys Gly Leu Thr Gly
        515                 520                 525 aaa ctc gac gca aga aaa atc aga gag atc ctc ata aag gcc aag aag    1632
Lys Leu Asp Ala Arg Lys Ile Arg Glu Ile Leu Ile Lys Ala Lys Lys
    530                 535                 540 ggc gga aag atc gcc gtg taattctaga gtcggggcgg ccggccgctt           1680
Gly Gly Lys Ile Ala Val
545                 550 cgagc                                                              1685
```

<210> SEQ ID NO 6
<211> LENGTH: 550
<212> TYPE: PRT
<213> ORGANISM: Artificial Sequence
<220> FEATURE:
<221> NAME/KEY: VARIANT
<222> LOCATION: (1)...(550)
<223> OTHER INFORMATION: Xaa = Any Amino Acid
<223> OTHER INFORMATION: Red shifted luciferase mutation

<400> SEQUENCE: 6

```
Xaa Xaa Xaa Xaa Xaa Xaa Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30
```

```
Tyr Ala Leu Val Pro Gly Thr Ile Ala Phe Thr Asp Ala His Ile Glu
         35                  40                  45

Val Asp Ile Thr Tyr Ala Glu Tyr Phe Glu Met Ser Val Arg Leu Ala
         50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
                100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
        130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
        210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Met Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
        290                 295                 300

Asp Leu Ser Asn Leu His Glu Ile Ala Ser Gly Gly Ala Pro Leu Ser
305                 310                 315                 320

Lys Glu Ile Ser Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Ser Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
```

-continued

```
                  450                 455                 460
Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ile Ala Val
545                 550
```

<210> SEQ ID NO 7
<211> LENGTH: 1686
<212> TYPE: DNA
<213> ORGANISM: pGL3
<220> FEATURE:
<221> NAME/KEY: CDS
<222> LOCATION: (1)...(1650)

<400> SEQUENCE: 7

```
atg gaa gac gcc aaa aac ata aag aaa ggc ccg gcg cca ttc tat ccg      48
Met Glu Asp Ala Lys Asn Ile Lys Lys Gly Pro Ala Pro Phe Tyr Pro
  1               5                  10                  15 ctg gaa gat gga acc gct gga gag caa ctg cat aag gct atg aag aga      96
Leu Glu Asp Gly Thr Ala Gly Glu Gln Leu His Lys Ala Met Lys Arg
             20                  25                  30 tac gcc ctg gtt cct gga aca att gct ttt aca gat gca cat atc gag    144
Tyr Ala Leu Val Pro Gly Thr Ile Ala Phe Thr Asp Ala His Ile Glu
         35                  40                  45 gtg gac atc act tac gct gag tac ttc gaa atg tcc gtt cgg ttg gca    192
Val Asp Ile Thr Tyr Ala Glu Tyr Phe Glu Met Ser Val Arg Leu Ala
     50                  55                  60 gaa gct atg aaa cga tat ggg ctg aat aca aat cac aga atc gtc gta    240
Glu Ala Met Lys Arg Tyr Gly Leu Asn Thr Asn His Arg Ile Val Val
 65                  70                  75                  80 tgc agt gaa aac tct ctt caa ttc ttt atg ccg gtg ttg ggc gcg tta    288
Cys Ser Glu Asn Ser Leu Gln Phe Phe Met Pro Val Leu Gly Ala Leu
                 85                  90                  95 ttt atc gga gtt gca gtt gcg ccc gcg aac gac att tat aat gaa cgt    336
Phe Ile Gly Val Ala Val Ala Pro Ala Asn Asp Ile Tyr Asn Glu Arg
            100                 105                 110 gaa ttg ctc aac agt atg ggc att tcg cag cct acc gtg gtg ttc gtt    384
Glu Leu Leu Asn Ser Met Gly Ile Ser Gln Pro Thr Val Val Phe Val
        115                 120                 125 tcc aaa aag ggg ttg caa aaa att ttg aac gtg caa aaa aag ctc cca    432
Ser Lys Lys Gly Leu Gln Lys Ile Leu Asn Val Gln Lys Lys Leu Pro
    130                 135                 140 atc atc caa aaa att att atc atg gat tct aaa acg gat tac cag gga    480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt    528
Phe Gln Ser Met Tyr Thr Phe Val Thr Ser His Leu Pro Pro Gly Phe
                165                 170                 175 aat gaa tac gat ttt gtg cca gag tcc ttc gat agg gac aag aca att    576
Asn Glu Tyr Asp Phe Val Pro Glu Ser Phe Asp Arg Asp Lys Thr Ile
            180                 185                 190
```

-continued

```
gca ctg atc atg aac tcc tct gga tct act ggt ctg cct aaa ggt gtc        624
Ala Leu Ile Met Asn Ser Ser Gly Ser Thr Gly Leu Pro Lys Gly Val
            195                 200                 205 gct ctg cct cat aga act gcc tgc gtg aga ttc tcg cat gcc aga gat        672
Ala Leu Pro His Arg Thr Ala Cys Val Arg Phe Ser His Ala Arg Asp
        210                 215                 220 cct att ttt ggc aat caa atc att ccg gat act gcg att tta agt gtt        720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg        768
Val Pro Phe His His Gly Phe Gly Met Phe Thr Thr Leu Gly Tyr Leu
                245                 250                 255 ata tgt gga ttt cga gtc gtc tta atg tat aga ttt gaa gaa gag ctg        816
Ile Cys Gly Phe Arg Val Val Leu Met Tyr Arg Phe Glu Glu Glu Leu
            260                 265                 270 ttt ctg agg agc ctt cag gat tac aag att caa agt gcg ctg ctg gtg        864
Phe Leu Arg Ser Leu Gln Asp Tyr Lys Ile Gln Ser Ala Leu Leu Val
        275                 280                 285 cca acc cta ttc tcc ttc ttc gcc aaa agc act ctg att gac aaa tac        912
Pro Thr Leu Phe Ser Phe Phe Ala Lys Ser Thr Leu Ile Asp Lys Tyr
290                 295                 300 gat tta tct aat tta cac gaa att gct tct ggt ggc gct ccc ctc tct        960
Asp Leu Ser Asn Leu His Glu Ile Ala Ser Gly Gly Ala Pro Leu Ser
305                 310                 315                 320 aag gaa gtc ggg gaa gcg gtt gcc aag agg ttc cat ctg cca ggt atc       1008
Lys Glu Val Gly Glu Ala Val Ala Lys Arg Phe His Leu Pro Gly Ile
                325                 330                 335 agg caa gga tat ggg ctc act gag act aca tca gct att ctg att aca       1056
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt       1104
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt       1152
Phe Glu Ala Lys Val Val Asp Leu Asp Thr Gly Lys Thr Leu Gly Val
370                 375                 380 aat caa aga ggc gaa ctg tgt gtg aga ggt cct atg att atg tcc ggt       1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga       1248
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc       1296
Trp Leu His Ser Gly Asp Ile Ala Tyr Trp Asp Glu Asp Glu His Phe
            420                 425                 430 ttc atc gtt gac cgc ctg aag tct ctg att aag tac aaa ggc tat cag       1344
Phe Ile Val Asp Arg Leu Lys Ser Leu Ile Lys Tyr Lys Gly Tyr Gln
        435                 440                 445 gtg gct ccc gct gaa ttg gaa tcc atc ttg ctc caa cac ccc aac atc       1392
Val Ala Pro Ala Glu Leu Glu Ser Ile Leu Leu Gln His Pro Asn Ile
450                 455                 460 ttc gac gca ggt gtc gca ggt ctt ccc gac gat gac gcc ggt gaa ctt       1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa       1488
Pro Ala Ala Val Val Val Leu Glu His Gly Lys Thr Met Thr Glu Lys
                485                 490                 495 gag atc gtg gat tac gtc gcc agt caa gta aca acc gcg aaa aag ttg       1536
Glu Ile Val Asp Tyr Val Ala Ser Gln Val Thr Thr Ala Lys Lys Leu
            500                 505                 510
```

```
cgc gga gga gtt gtg ttt gtg gac gaa gta ccg aaa ggt ctt acc gga    1584
Arg Gly Gly Val Val Phe Val Asp Glu Val Pro Lys Gly Leu Thr Gly
            515                 520                 525 aaa ctc gac gca aga aaa atc aga gag atc ctc ata aag gcc aag aag    1632
Lys Leu Asp Ala Arg Lys Ile Arg Glu Ile Leu Ile Lys Ala Lys Lys
        530                 535                 540 ggc gga aag atc gcc gtg taattctaga gtcggggcgg ccggccgctt           1680
Gly Gly Lys Ile Ala Val
545                 550 cgagca                                                              1686
```

<210> SEQ ID NO 8
<211> LENGTH: 550
<212> TYPE: PRT
<213> ORGANISM: pGL3

<400> SEQUENCE: 8

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300
```

```
Asp Leu Ser Asn Leu His Glu Ile Ala Ser Gly Ala Pro Leu Ser
305                 310                 315                 320

Lys Glu Val Gly Glu Ala Val Ala Lys Arg Phe His Leu Pro Gly Ile
            325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
    435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ile Ala Val
545                 550

<210> SEQ ID NO 9
<211> LENGTH: 4233
<212> TYPE: DNA
<213> ORGANISM: Luciola lateralis

<400> SEQUENCE: 9
aagcttcacg tgtcgttgtt cctcgaataa aactaagaca aaaattcctt tgcaaaaaac        60
taaaatctcc taacctgacg actgtagtgg gctggagcgc catcatgctg gtatattaaa       120
ttgtgtctaa tatctagtgt tacatcttta agcaaaactg gaagtatttt attaagaaaa       180
tgtagataat ttctggcatt tcatgtattg ggtaagaaat gtggtccaac tattctggtt       240
caaattattc ccagccaaac attcaatgaa aacgatgtt gatggccaaa gtctagccaa        300
taaccaattg attgcaaaaa tttactcttt gccgataatc cgcaggtaac aaaggctgta       360
ttttacggaa cctgtaagga tattaatgat catcttttaa gacttgatga actgtcttat       420
tgctgttaat gttaaacaat cttgcaattc ccctagtact acaccgagga tcttcagcga       480
cagcatttag aattgcttgc tcctgattag gtgtgcgtcg agttcgtggt cgccctgtat       540
cccttcttat tggtattaca cgtccagttt tccttaatct tctatctaac ctcgtaaata       600
cgtgtctcga cgagcaggaa atcttctgga atactcagca ggacaatcaa aacgttctaa       660
```

```
gtacataaac cgtcaacaat ctcaaacttt acaatagaag cgtcgcttgc tagatgacag    720
cactaatttt gcgcaatctt aaaatataaa aaacaaattt tgtaaattaa aatacgattg    780
gttttactta agcctaattt agtaaaaaaa acatttttct cacaaaattg agcaagttgc    840
cagataaaat atgcaatgct aaactaattt tagacaaaca gtattaaact ttaaaaattc    900
atatcattat gcagatcagt aaaagatctt agctgaaaca tctacataat atgaaaaatg    960
tttcttatat tgtaagaaat tttgacgttg aattatatac aagtagtaaa cttttgtaa     1020 tgaattttct gaataaaagt aataacatct aagagaccaa atagaataaa ggtcttgtac    1080
cagacacata gacgttaagg tgtagttatt gtgatgatag tataagttca ataaacaaat    1140 tactttatt caaatttagc ggttaaagta attgaacttt attgaaagaa atattcgag      1200 tcgtaatgta taaaattaaa gtttaaaatg catacttaca acatttaaaa aattaattgc    1260
actgtagagt gaaccattag aagtagcgtt tactcatata actgtcgttt actatgatca    1320
aagtttctac gtacaaaaag ttacataaaa cataaaattt aaatattctt tattatagta    1380
taaaattagc aaatagacat tatttttata acattgttaa cagaagcata cattaaaata    1440
tctaataaaa attaatgatc cattaagata tacaaaaaac caatacatttt ttttaaatg    1500 tcgaaaataa ttcattacat taattgctta gtataaattta agcatttatt ttaaaattgt   1560
tttaaaatgt ttgtgctttt tttaaccagt tagacgttag atatcatcgt tgttgttaca    1620
atcgtataac acgctaacat tatgaaacac aaaataattt tttataggta ttttagtttt    1680
acttgcttgt aaaattatta ttttttacta taaatttaat gagacgatta aggatcaagg    1740
gtctagtacc cgatatattt aatcggaggt agagttcgtt aagtactctt gtagtggagt    1800
gtttagttac aagtgcggct tgaaaacgat taataaacct ttttttaaaa aatggaaaac    1860
atggataacg atgaaaatat tgtatatggt cctaaaccat tttacccat tgaagaggga     1920 tctgctggag cacaattgcg caagtatatg gatcgatatg caaaacttgg cgcaattgct    1980
tttgtaagtt cattatgtga aattaatttt tataaaaaaa actcttctaa actcaatttt    2040
tgtattaaat taaaatttag actaacgcac ttaccggtgt cgattatacg tacgccgaat    2100
acttagaaaa atcatgctgt ctaggagagg ctttaaagaa ttatggtttg gttgttgatg    2160
gaagaattgc gttatgcagt gaaaactgtg aagaattttt tattcctgta ttagccggat    2220
tatttatagg tgtcggtgtg gctccaacta atgagattta cactctgcgt aagcatctat    2280
acgtttagta gaacgtagta tttacagtaa acaattttt aggtgaattg gttcacagtt     2340
taggaatctc taagccaaca attgtattta gttctaaaaa aggattagat aaagttataa    2400
ctgtacaaaa aacggtaact gctattaaaa ccattgttat attggacagc aaggtggatt    2460
atagaggata tcaatcaatg gacaacttta ttaaaaaaaa cactccacca ggtttcaaag    2520
gatcaagttt taaaactgta gaagttaacc gcaaagaaca agttgctctc ataatgaact    2580
cttcgggttc caccggtttg ccaaaaggtg tgcaacttac tcacgaaaat gcagtcacta    2640
gattttctca cgctaggtac ttattagtta tatagtaaaa agtctatatt tatactttt     2700 attagagatc caatttatgg aaatcaagtt tcaccaggca cggctatttt aactgtagta    2760
ccattccatc atggttttgg tatgtttact actttaggct atctaacttg tggttttcgt    2820
attgtcatgt taacaaaatt tgacgaagaa acgtttttaa aaacactgca agattacaaa    2880
tgttcaagtg ttattcttgt accgaccttg tttgcaattc ttaatagaag tgaattactc    2940
gataaatatg atttatcaaa tttagttgaa attgcatctg gcggagcacc tttatcaaaa    3000
gaaattggtg aagctgttgc tagacggtag cttttttttt ttaatttta gtcaaatatt     3060
```

-continued

```
ttataaatct atttcagttt taatttaccg ggtgttcgtc aaggctatgg tttaacagaa    3120
acaacctctg caattattat tacaccagaa ggcgatgata aaccaggtgc ttctggaaaa    3180
gttgtgccat tatttaaagc aaaagttatc gatcttgata ccaaaaaaac tttgggcccg    3240
aacagacgtg gagaagtttg tgtaaaaggt cctatgctta tgaaggtta tgtagataat    3300 ccagaagcaa caagagaaat tatagatgaa gaaggttggt tgcacacagg agatattggg    3360
tattacgatg aagaaaaaca ttttttttatc gtggatcgtt tgaagtcttt aatcaaatac    3420
aaaggatatc aagtaatatt ttttaaccga taaaaataat tctaaatatt taatttaggt    3480
acctcctgct gaattagaat ctgttctttt gcaacatcca aatattttg atgccggcgt    3540 tgctggcgtt ccagatccta tagctggtga gcttccggga gctgttgttg tacttgaaaa    3600
aggaaaatct atgactgaaa aaaagtaat ggattacgtt gcaggtaact actattcaac    3660
acaagttaaa aaaatactat tacatttttt gtgtaggtca agtttcaaat gcaaaacgtt    3720
tgcgtggtgg tgtccgtttt gtggacgaag tacctaaagg tcttactggt aaaattgatg    3780
gtaaagcaat tagagaaata ctaaagaaac cagttgctaa gatgtaaatg tcaatcaatc    3840
gtttaatcaa attattaaag aaatgactac atttaatgtt ttactcatttttttttttaa    3900 attaagtggg attcaaatcg tttatactga tactttacca agtagatgat taaattactt    3960
tattatataa atgttttatc aaataagtac gacttttgta atttactcga gtgggcgtac    4020 tttttattatt attgattata tttctaaaac ttgtgtacgt tacgcaaaaa ttatccaaaa    4080
aatataattt aatattatta tctctttgtt ttacaatatt tatgacaaaa agtaacatt    4140 tattggaaat aaagtaattt ctgttattat caaatggcgt atagtgatgc aaaataatta    4200
tagacaccga ttcaaaattt ttgctcaaag ctt                                 4233
```

<210> SEQ ID NO 10
<211> LENGTH: 548
<212> TYPE: PRT
<213> ORGANISM: Luciola lateralis

<400> SEQUENCE: 10

```
Met Glu Asn Met Asp Asn Asp Glu Asn Ile Val Tyr Gly Pro Lys Pro
 1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160
```

```
Arg Gly Tyr Gln Ser Met Asp Asn Phe Ile Lys Lys Asn Thr Pro Pro
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Leu Glu Lys Gly Lys Ser Met Thr
                485                 490                 495

Glu Lys Lys Val Met Asp Tyr Val Ala Gly Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Met
545

<210> SEQ ID NO 11
<211> LENGTH: 2387
<212> TYPE: DNA
```

<213> ORGANISM: Photinus pyralis

<400> SEQUENCE: 11

```
ctgcagaaat aactaggtac taagcccgtt tgtgaaaagt ggccaaaccc ataaatttgg      60
caattacaat aaagaagcta aaattgtggt caaactcaca acattttta ttatatacat     120
tttagtagct gatgcttata aaagcaatat ttaaatcgta acaacaaat aaataaaat     180
ttaaacgatg tgattaagag ccaaaggtcc tctagaaaaa ggtatttaag caacggaatt     240
cctttgtgtt acattcttga atgtcgctcg cagtgacatt agcattccgg tactgttggt     300
aaaatggaag acgccaaaaa cataaagaaa ggcccggcgc cattctatcc tctagaggat     360
ggaaccgctg gagagcaact gcataaggct atgaagagat acgccctggt tcctggaaca     420
attgcttttg tgagtatttc tgtctgattt ctttcgagtt aacgaaatgt tcttatgttt     480
ctttagacag atgcacatat cgaggtgaac atcacgtacg cggaatactt cgaaatgtcc     540
gttcggttgg cagaagctat gaaacgatat gggctgaata caaatcacag aatcgtcgta     600
tgcagtgaaa actctcttca attctttatg ccggtgttgg gcgcgttatt tatcggagtt     660
gcagttgcgc ccgcgaacga catttataat gaacgtaagc accctcgcca tcagaccaaa     720
gggaatgacg tatttaattt ttaaggtgaa ttgctcaaca gtatgaacat ttcgcagcct     780
accgtagtgt ttgtttccaa aaaggggttg caaaaaattt tgaacgtgca aaaaaaatta     840
ccaataatcc agaaaattat tatcatggat tctaaaacgg attaccaggg atttcagtcg     900
atgtacacgt tcgtcacatc tcatctacct cccggtttta atgaatacga ttttgtacca     960
gagtcctttg atcgtgacaa acaattgca ctgataatga attcctctgg atctactggg    1020
ttacctaagg gtgtggccct tccgcataga actgcctgcg tcagattctc gcatgccagg    1080
tatgtcgtat aacaagagat taagtaatgt tgctacacac attgtagaga tcctattttt    1140
ggcaatcaaa tcattccgga tactgcgatt ttaagtgttg ttccattcca tcacggtttt    1200
ggaatgttta ctacactcgg atatttgata tgtggatttc gagtcgtctt aatgtataga    1260
tttgaagaag agctgttttt acgatccctt caggattaca aaattcaaag tgcgttgcta    1320
gtaccaaccc tattttcatt cttcgccaaa agcactctga ttgacaaata cgatttatct    1380
aatttacacg aaattgcttc tggggggcgca cctctttcga aagaagtcgg ggaagcggtt    1440
gcaaaacggt gagttaagcg cattgctagt atttcaaggc tctaaaacgg cgcgtagctt    1500
ccatcttcca gggatacgac aaggatatgg gctcactgag actacatcag ctattctgat    1560
tacacccgag ggggatgata aaccgggcgc ggtcggtaaa gttgttccat tttttgaagc    1620
gaaggttgtg gatctggata ccgggaaaac gctgggcgtt aatcagagag gcgaattatg    1680
tgtcagagga cctatgatta tgtccggtta tgtaaacaat ccggaagcga ccaacgcctt    1740
gattgacaag gatggatggc tacattctgg agacatagct tactgggacg aagacgaaca    1800
cttcttcata gttgaccgct tgaagtcttt aattaaatac aaaggatatc aggtaatgaa    1860
gattttttaca tgcacacacg ctacaatacc tgtaggtggc cccgctgaa ttggaatcga    1920
tattgttaca acaccccaac atcttcgacg cgggcgtggc aggtcttccc gacgatgacg    1980
ccggtgaact tcccgccgcc gttgttgttt tggagcacgg aaagacgatg acggaaaaag    2040
agatcgtgga ttacgtcgcc agtaaatgaa ttcgttttac gttactcgta ctacaattct    2100
tttcataggt caagtaacaa ccgcgaaaaa gttgcgcgga ggagttgtgt ttgtggacga    2160
agtaccgaaa ggtcttaccg gaaaactcga cgcaagaaaa atcagagaga tcctcataaa    2220
ggccaagaag ggcggaaagt ccaaattgta aaatgtaact gtattcagcg atgacgaaat    2280
```

```
tcttagctat tgtaatatta tatgcaaatt gatgaatggt aattttgtaa ttgtgggtca    2340
ctgtactatt ttaacgaata ataaaatcag gtataggtaa ctaaaaa               2387
```

<210> SEQ ID NO 12
<211> LENGTH: 550
<212> TYPE: PRT
<213> ORGANISM: Photinus pyralis

<400> SEQUENCE: 12

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350
```

-continued

```
Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
        530                 535                 540

Gly Gly Lys Ser Lys Leu
545             550
```